(12) United States Patent
Malet et al.

(10) Patent No.: US 10,849,316 B2
(45) Date of Patent: Dec. 1, 2020

(54) APPARATUS AND METHOD TO DETECT UPSIDE DOWN EGGS

(71) Applicant: EGG-CHICK AUTOMATED TECHNOLOGIES, Landivisiau (FR)

(72) Inventors: Bertrand Malet, Guiclan (FR); Laura Trubuil, Pont Melvez (FR); Maharavo Andriamiarisoa, Landivisiau (FR)

(73) Assignee: EGG-CHICK AUTOMATED TECHNOLOGIES, Landivisiau (FR)

( * ) Notice: Subject to any disclaimer, the term of this patent is extended or adjusted under 35 U.S.C. 154(b) by 0 days.

(21) Appl. No.: 16/075,832

(22) PCT Filed: Feb. 7, 2017

(86) PCT No.: PCT/IB2017/000160
§ 371 (c)(1),
(2) Date: Aug. 6, 2018

(87) PCT Pub. No.: WO2017/137837
PCT Pub. Date: Aug. 17, 2017

(65) Prior Publication Data
US 2019/0037814 A1    Feb. 7, 2019

Related U.S. Application Data

(60) Provisional application No. 62/292,554, filed on Feb. 8, 2016.

(51) Int. Cl.
*A01K 43/04* (2006.01)
*A01K 43/00* (2006.01)
*B65B 23/06* (2006.01)

(52) U.S. Cl.
CPC .............. *A01K 43/04* (2013.01); *A01K 43/00* (2013.01); *B65B 23/06* (2013.01)

(58) Field of Classification Search
CPC .......... B65B 23/06; A01K 43/00; A01K 43/04
(Continued)

(56) References Cited

U.S. PATENT DOCUMENTS 5,014,339 A * 5/1991 Tattermusch ........ H05B 3/0052
392/491
6,234,320 B1    5/2001 Hebrank
(Continued)

FOREIGN PATENT DOCUMENTS

AU    2013 216 684 A1    9/2013
JP    2014-60957 A    4/2014
(Continued)

OTHER PUBLICATIONS

Korean Office Action dated Aug. 30, 2019 in Korean Patent Application No. 10-2018-7022686 (with English translation), citing documents AO and AP therein, 26 pages.
(Continued)

*Primary Examiner* — Terrell H Matthews
(74) *Attorney, Agent, or Firm* — Oblon, McClelland, Maier & Neustadt, L.L.P.

(57) ABSTRACT

An apparatus to identify upside-down eggs of a batch of eggs includes a heating module configured to expose an air cell in each egg of the batch of eggs to a radiation flux. The apparatus also includes an imaging module with a thermal camera configured to capture thermal images of the batch of eggs when the eggs are not exposed to the radiation flux. The apparatus further includes an analyzer module configured to detect the presence of a heated zone in the air cell of each egg from the thermal images and identify upside-down eggs based on the presence of the heated zone. A method to identify upside-down eggs from a batch of eggs includes heating the batch of eggs with a radiation source, such as an infrared source, so as to generate a hot zone inside an air cell (Continued)

of each egg without significantly heating the rest of the eggs. Thermal images of the eggs are captured while the eggs are not exposed to the radiation source, analyzed to detect the presence of the hot zone and to identify the upside down eggs.

21 Claims, 5 Drawing Sheets

(58) Field of Classification Search
USPC .................................. 209/509, 510, 511, 546
See application file for complete search history.

(56) References Cited

U.S. PATENT DOCUMENTS

| | | | |
|---|---|---|---|
| 2002/0014444 A1 | 2/2002 | Hebrank | |
| 2008/0302707 A1* | 12/2008 | Bourely | B07C 5/34 209/577 |
| 2011/0131829 A1* | 6/2011 | Zagar | F26B 3/283 34/274 |
| 2012/0182543 A1* | 7/2012 | De Baerdemaeker | G01G 9/00 356/54 |

FOREIGN PATENT DOCUMENTS

| | | | | |
|---|---|---|---|---|
| JP | 2014060957 A * | 4/2014 | ............. | A01K 43/00 |
| KR | 10-2004-0062687 A | 7/2004 | | |
| WO | WO-2008088382 A1 * | 7/2008 | ........... | G01N 33/085 |
| WO | WO 2008/096236 A1 | 8/2008 | | |
| WO | WO-2008096236 A1 * | 8/2008 | ........... | G01N 33/085 |

OTHER PUBLICATIONS

European Office Action dated Sep. 10, 2019 in European Patent Application No. 17715524.9, 5 pages.
International Search Report dated May 30, 2017, in PCT/IB2017/000160 filed Feb. 7, 2017.
Written Opinion of the International Searching Authority dated May 30, 2017, in PCT/IB2017/000160 filed Feb. 7, 2017.
Office Action dated Sep. 20, 2018 in European Patent Application No. 17715524.9, 3 pages.

* cited by examiner

APPARATUS AND METHOD TO DETECT UPSIDE DOWN EGGS

CROSS-REFERENCE TO RELATED APPLICATIONS

This application is related to U.S. provisional Ser. No. 62/292,554, filed Feb. 8, 2016, entitled "APPARATUS AND METHOD TO DETECT UPSIDE DOWN EGGS", the entire contents of which are hereby incorporated by reference.

BACKGROUND

Field of the Disclosure

The present disclosure relates generally to egg processing and more specifically to an apparatus and method to detect upside down eggs.

Description of the Related Art

In the poultry industry and especially in hatcheries, the eggs that need to be treated are placed in trays equipped with cells. Eggs are conventionally disposed in the cells of the tray in an upright position, i.e., the air cell present in the egg is facing upward. Most egg processings, e.g. incubation, hatching, and in ovo injection, are designed to be performed on eggs placed in the upright position.

For example in in ovo injections, various substances, such as vaccines or nutrients, are conventionally injected into the egg via a needle piercing through the shell, the air cell, and delivering the substances inside the amnion. Such injection techniques are typically employed in the commercial poultry industry to decrease post-hatch mortality rates or increase growth rates of hatched birds.

If an in ovo injection is performed on an upside down egg, the embryo and yolk rather than the air cell may be pierced by the needle which may damage or kill the embryo.

Unfortunately, due to the shape of the egg, it can be difficult to determine whether an egg is in an upright position. To remedy to this problem several conventional apparatuses have been disclosed.

These conventional apparatuses use the candling technique to determine the air cell position inside the egg, and consequently detect if the egg is in an upside down position. The candling technique uses a bright light source behind the egg to show details through the shell, and notably the air cell position. This technique is so called because the original sources of light used were candles.

Most of these conventional apparatuses include a plurality of photodetectors and a plurality of photoemitters configured to be positioned on opposite sides of each egg contained in a tray. A light beam is emitted from each photoemitter and the corresponding photodetector monitors the intensity of the refraction of the light beam through the egg to detect the location of the air cell.

Though such conventional apparatuses have achieved success in detecting eggs in the upside down position, they have numerous shortcomings. Due to their complex designs that rely on numerous photoemitters and corresponding photodetectors, these apparatuses are prone to failure and/or inaccurate detections and may end up slowing down the process. For example, misalignment between the eggs and the plurality of emitters and detectors may provide inaccurate results. In addition, the plurality of photoemitters and corresponding photodetectors are often arranged such that all the eggs inside the tray cannot be processed in one single step but rather line by line which reduces the rapidity of the detection.

Thus, an apparatus and method capable of accurately and rapidly detecting upside down eggs are desired.

SUMMARY

Accordingly, an object of the present disclosure is to provide an apparatus and a method to detect upside down eggs which overcome or mitigate at least some of the above-mentioned limitations.

The apparatus and method of the present disclosure address the limitations of accuracy and rapidity by exploiting the low thermal inertia of the air cell present in the egg compared to the other constituents of the egg.

The proposed apparatus and method are configured to expose a batch of eggs to a tailored heat flux such that only the temperature inside air cells of the eggs is substantially increased while the temperature inside the other parts of the eggs remain substantially unchanged. Such a tailored heat flux can be transmitted through shortwave infrared light produced by a heating module with infrared coating (IRC) lamps that expose the eggs.

In addition, through thermal image processing the apparatus and method enable to efficiently detect on which part of the egg (e.g., the top or bottom) the substantial temperature increase is located and consequently detect that the egg is in an upside down position.

A non-limiting illustrative example is directed to an apparatus to detect upside down eggs, the apparatus including a heating module comprising an infrared light source configured to expose the batch of eggs to an infrared light and create a hot zone in an air cell of each egg. The apparatus further includes an imaging module with a thermal camera configured to capture thermal images of the batch of eggs. The apparatus also includes an analyzer module configured to detect the presence of the hot zone in the air cell of each egg from the thermal images and identify the orientation of each egg in the batch of eggs. The apparatus can also include a conveyor system to move the eggs from the infrared light source to the thermal camera. The conveyor can stop the eggs at the infrared light source and/or at the thermal camera; or alternatively, the conveyor can keep the eggs moving during the heating of the eggs and their imaging in order to optimize the rate for processing the eggs, Another non-limiting illustrative example is directed to a method for identifying upside-down eggs from a batch of eggs. The method includes heating the batch of eggs with a radiation source, such as for example a short wave infrared light lamp. The method also incudes generating a hot zone inside an air cell of each egg via the radiation source. In a preferred embodiment, the other constituents of the eggs are not significantly heated by the infrared light lamp. The heating of the batch of eggs with the radiation source can then be stopped, for example by moving the eggs away from the radiation source. The method also includes capturing thermal images of the batch of eggs with a thermal camera while the heating of the batch of eggs is stopped, for example while the eggs are moving away from the radiation source and moving above the thermal camera. The thermal images are then analyzed to detect the presence of the hot zone; and the upside down eggs are detected.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
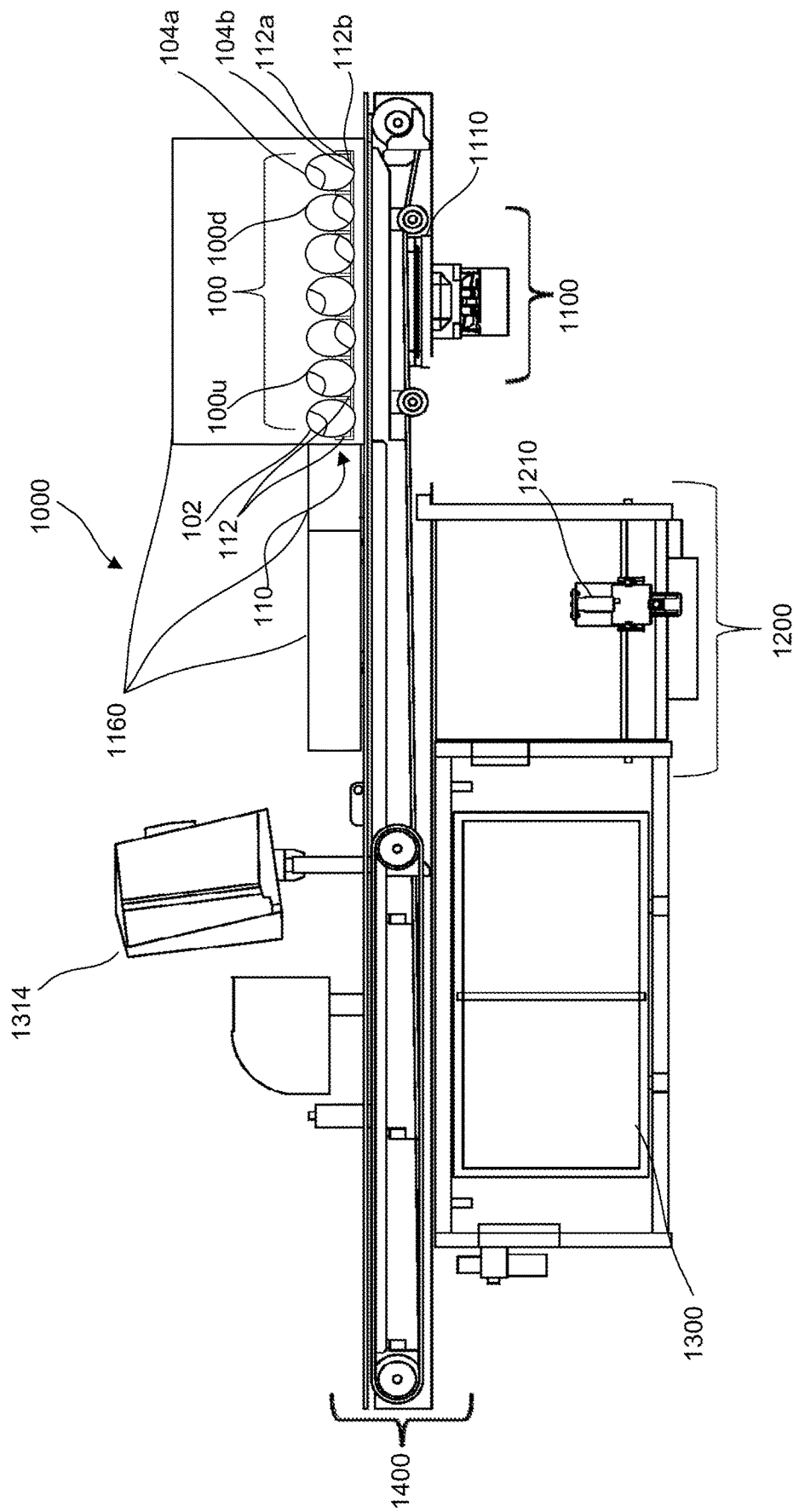
FIG. 1 is a sectional view of an apparatus to detect upside down eggs from a batch of eggs contained in a tray, according to certain aspects of the disclosure.

All systems, materials, methods, and examples discussed herein are illustrative only and are not intended to be limiting.

In the drawings, like reference numerals designate identical or corresponding parts throughout the several views. Further, as used herein, the words "a", "an", and the like include a meaning of "one or more", unless stated otherwise. The drawings are generally drawn not to scale unless specified otherwise or illustrating schematic structures or flowcharts.

FIG. 1 is a sectional view of an apparatus 1000 to detect an upside down egg 100d from a batch of eggs 100 contained in a tray 110, according to certain aspects of the disclosure.

The tray 110 containing the batch of eggs 100 includes a plurality of cells 112, wherein each cell of the plurality of cells 112 is designed to hold one egg 100. Each cell 112 is characterized by a first opening 112a and a second opening 112b. The first opening 112a exposes a first extremity 104a of the egg 100 in an upward direction, while the second opening 112b exposes a second extremity 104b of the egg 100 in a downward direction.

Each egg 100 includes an air cell 102 that may be located either in the first extremity 104a or in the second extremity 104b. When the air cell 102 is located in the first extremity 104a, the egg 100 is in the upright position, as illustrated in FIG. 1 by the egg 100u. When the air cell 102 is located in the second extremity 104b, the egg 100 is in the upside down position, as illustrated in FIG. 1 by the egg 100d.

The apparatus 1000 includes a conveyor system 1400, a heating module 1100, an imaging module 1200, and an analyzer module 1300 to perform thermal image processing.

The conveyor system 1400 conveys the tray 110 containing the batch of eggs 100 along a conveyance path passing through the top of the heating module 1100 and the top of the imaging module 1200.

The heating module 1100 is configured and operated to provide a detectable temperature increase of the air cell 102 while the temperature increases of other parts of the egg 100, e.g. amnion, yolk, embryo, and allantois, are significantly less or even negligible Such a difference in thermal behaviors is possible due to an important thermal inertia difference between the air cell 102 and the other parts of the egg 100.

The heating module 1100 exposes the batch of eggs 100 with a punctual and fast heat flux to generate a hot zone generally confined to the air cell 102 of each egg 100 and detectable by the imaging module 1200. To generate such a hot zone inside the air cell 102, parameters of the heat flux such as an exposure period and an exposure temperature may be adjusted. For example, the exposure temperature may be around 60° C. and the exposure time may be between 1 and 9 seconds.

The conveyor system 1400 displaces the batch of eggs 100 from the heating module 1100 to the imaging module 1200 where thermal images of the batch of eggs 100, after heat exposures, are captured by at least one thermal camera 1210 of the imaging module 1200.

An analyzer module 1300, that may be placed inside an electrical cabinet next to the imaging 1200, receives and executes software instructions to analyze the thermal images and detect the upside down eggs 100d in the batch of eggs 100. In a non-limiting embodiment, one or more covers 1160 can be placed above the eggs. The cover(s) 1160 can be configured to reduce heat loss during the heating step and/or during the imaging step.

Figure 2:
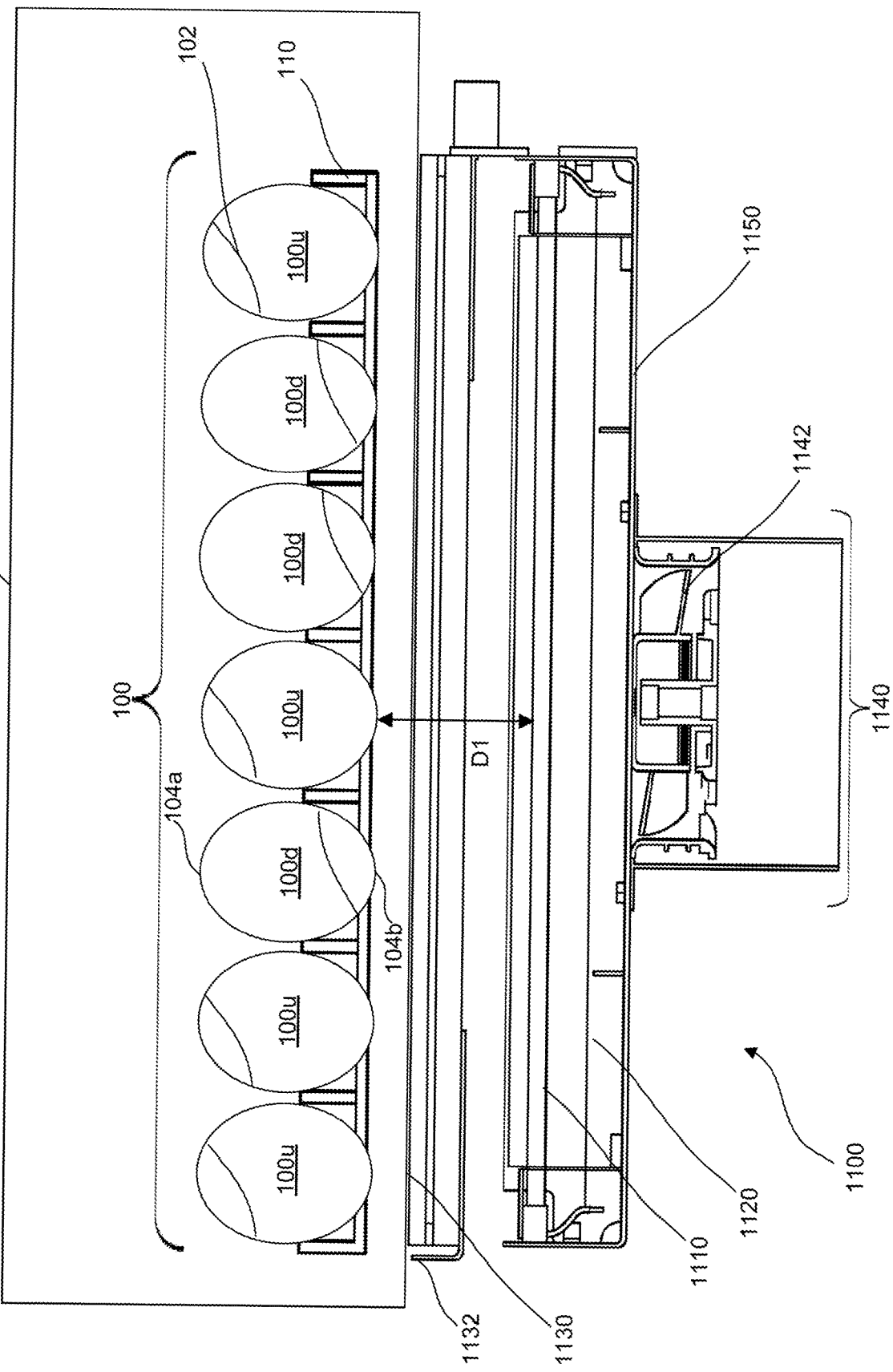
FIG. 2 is a sectional view of the heating module of the apparatus to detect the upside down eggs from the batch of eggs contained in the tray, according to certain aspects of the disclosure.

FIG. 2 is a sectional view of the heating module 1100 of the apparatus 1000, according to certain aspects of the disclosure.

In a non-limiting embodiment, the heating module 1100 includes one or more lamps 1110, reflectors 1120, a screen 1130, a cooling system 1140, and a support structure 1150.

The lamps 1110 and the reflectors 1120 are configured to project shortwave infrared light on the batch of eggs 100.

The lamps 1110 and the reflectors 1120 may extend along or across a longitudinal direction of the tray 110. The orientation and number of lamps depends on the size and other properties of the tray, the speed of tray, the types of eggs, etc. In a non-limiting embodiment, a pair of lamps are oriented along the moving direction.

The lamps 1110 may be infrared coating (IRC) lamps that emit infrared wave with a width length between 0.76 to 2.00 μm to provide a maximum power in a minimum exposure period, e.g. 1 second. For example, the lamps can include one or more commercially available infrared halogen lamps of 1000 W.

In addition, the lamps 1110 can be placed at an exposure distance D1 from the tray 110 to tailor the heat flux received by the batch of eggs 100. The exposure distance D1 may be adjusted depending on different factors, e.g. type of tray 110, speed of the tray 110 on the conveyor system 1400, number of eggs, the number of lamps, egg sizes and/or ambient temperature. For example, the exposure distance D1 may vary from 60 mm to 200 mm for a pair of lamps 1110 with a nominal lamp power between 500 W and 5000 W.

The reflectors 1120 are placed below the lamps 1110 to limit heat waste and to direct the shortwave infrared light on the batch of eggs 100. The reflectors 1120 may be made of reflective materials capable of withstanding high temperatures, e.g. temperatures above 60° C., such as polished aluminum alloys.

The screen 1130 may be placed between the lamps 1110 and the batch of eggs 100. The screen 1130 protects the lamps 1110 against detritus that can fall from the batch of eggs 100, e.g. feathers and shell pieces. The screen 1130 may be a glass panel designed to allow the shortwave infrared light to go through, for example the screen 1130 may be made from a mixture of silica and quartz.

In addition, the screen 1130 may be removably affixed to the support structure 1150 to be easily removed and cleaned. For example, the screen 1130 may be longitudinally inserted and withdrawn through a pair of rails 1132. The pair of rails 1132 may be placed above the at least one pair of lamps 1110 and may extend longitudinally along a length of the heating module 1100.

The heating module 1100 may also include a security system that prevents the use of the lamps 1110 when the screen 1130 is removed from the heating module 1100. For example, the security system may include an electrical switch that cuts the power supply to the lamps 1110 when the screen 1130 is removed, and reestablishes the power supply to the lamps 1110 when the screen 1130 is inserted on the heating module 1100.

The cooling system 1140 can be configured to extend the lifespan of the lamps 1110. The cooling system 1140 may rely on one or more fans 1142 placed below the heating module 1100. The fans 1142 can be configured to generate an air circulation from the top of the lamps 1110 to the bottom of the heating module 1100. The top to bottom direction of the air circulation is implemented to avoid hot air being sent toward the batch of eggs 100 and/or the imaging module 1200 and produce perturbations on the thermal images of the batch of eggs 100. Such an air circulation cools down both the lamps 1110 and the reflectors 1120.

The support structure 1150 may be a housing supporting the lamps 1110, the reflectors 1120, the screen 1130, and the cooling system 1140. The support structure 1150 may be made from rigid materials capable of withstanding high temperatures, e.g. temperatures above 60° C., such as stainless steel alloys.

Figure 3:
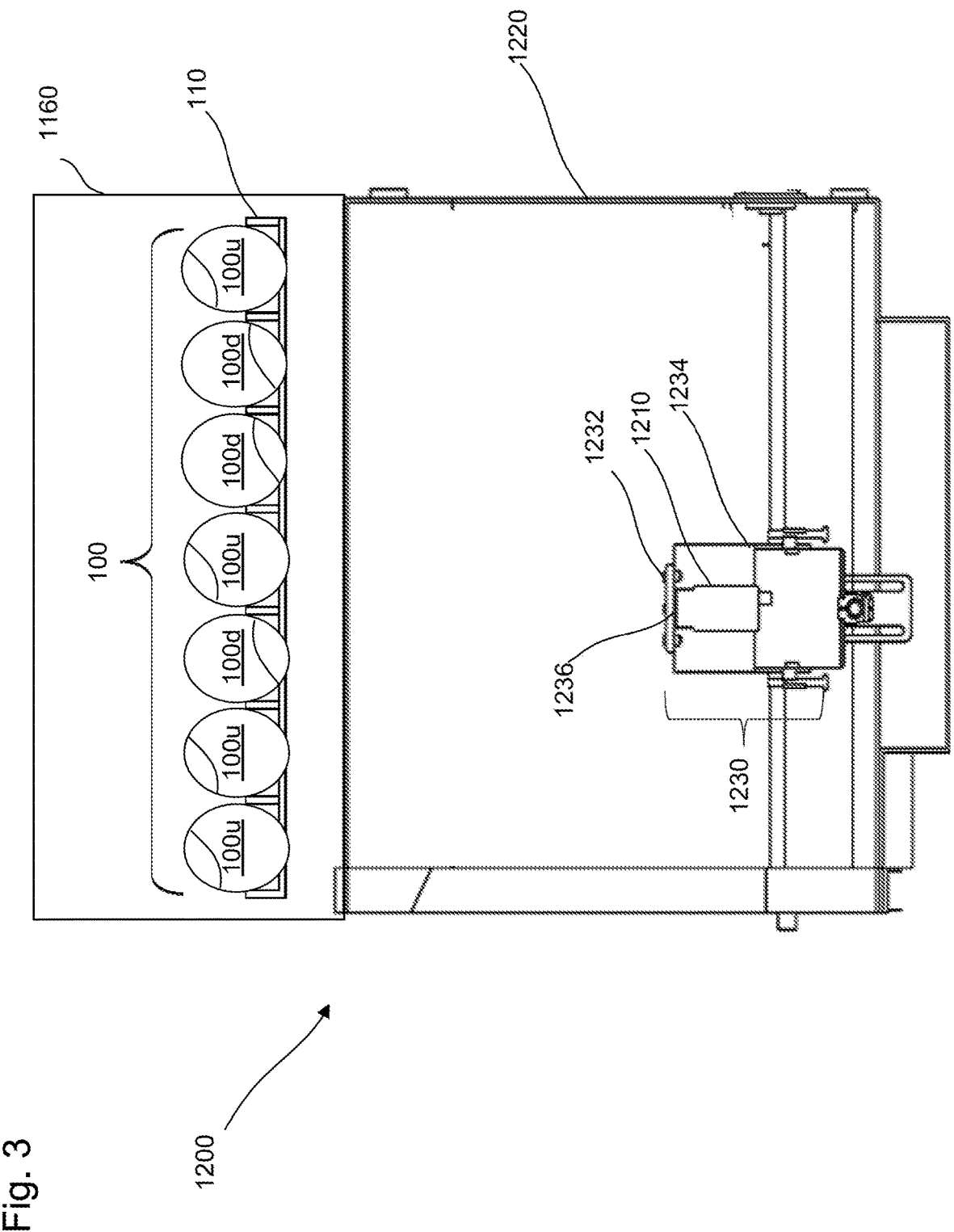
FIG. 3 is a sectional view of the imaging module of the apparatus to detect the upside down eggs from the batch of eggs contained in the tray, according to certain aspects of the disclosure.

FIG. 3 are a sectional view of the imaging module 1200, according to certain aspects of the disclosure.

The imaging module 1200 includes a housing 1220 containing one or more thermal cameras 1210 protected by a camera housing 1230. For example, the thermal camera(s) can be a commercially available infrared camera with an IR resolution of 640×512 pixels having a thermal sensitivity of less than 0.05° C. at 30° C. with an accuracy of 5% of reading; an F-number of 1.25 and a fixed focus.

The housing 1220 may be thermally isolated from the external environment to avoid thermal disturbance that may affect the thermal images of the batch of eggs 100. The thermal insulation of the housing 1220 is configured to act as a barrier to external thermal perturbations, e.g. air flow, and to provide a substantially uniform temperature distribution inside the housing 1220 with small temperature leaks. The housing 1220 may be made from rigid and isolating material such as isolated stainless steel alloys.

The camera housing 1230 may include a protection window 1232 supported by a plurality of panels 1234 affixed together to form an enclosure and protect the at least one thermal camera 1210 against external elements such as dust and/or moisture. The protection window 1232 may be placed on top of a lens 1236 of the thermal camera(s) 1210 and constructed to not disturb the quality of the thermal images captured by the thermal camera(s) 1210. For example, the protection window 1232 may be built from the Fluke CV series infrared window from FLUKE® and have dimensions corresponding to the lens 1236 of the thermal camera 1230.

The plurality of panels 1234 forming the camera housing 1230 may be made from heat conductive materials such as aluminum and/or stainless steel allows facilitating heat extraction from the camera 1210 and limit diffusion of thermal perturbations. Furthermore, the camera housing 1230 may also include a camera cooling system employing compressed air, water, forced ambient air, heat sinks or the combination thereof.

The camera housing 1230 may be mounted on a multi-axial positioning system to adjust the position of the thermal camera 1210 and the field of view. The multi-axial positioning system may rely on rack-and-pinion systems and/or ball and grip systems.

The thermal camera 1210 may have an object temperature range sufficiently large and thermal sensitivity sufficiently high to be able to detect the difference of temperature between the air cell 102 and the other parts of the egg 100, i.e., detect the hot zone generated in the air cell 102. For example, the thermal camera 1210 may have a minimum temperature range between 0° C. and 100° C. and a thermal sensitivity around 0.1° C. such as the FUR A35 from FLIR®).

Depending on the size of the tray 110 and the rate at which the tray 110 passes on top of the imaging module 1200, the thermal camera(s) 1210 can include up to eight thermal cameras, although more cameras are possible. In addition, the exposure distance D1 between the thermal camera 1210 and the batch of eggs 100 may be adjusted depending on the number of thermal cameras used and the field of view of each thermal camera.

Figure 4:
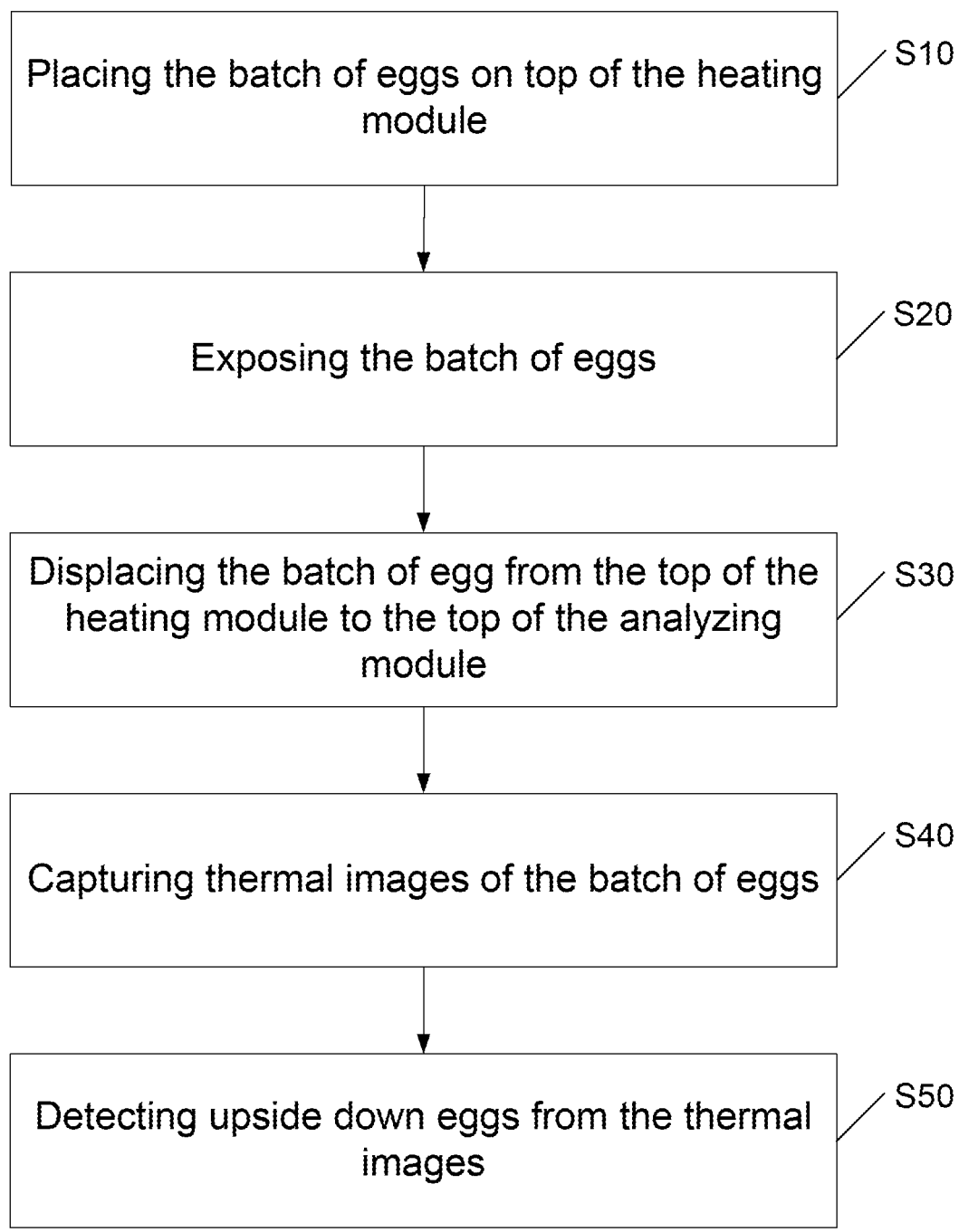
FIG. 4 is a flow chart of a method for detecting the upside down eggs from the batch of eggs contained in the tray, according to certain aspects of the disclosure.

FIG. 4 is a flow chart of a method for detecting an upside down egg 100d, according to certain aspects of the disclosure. In a step S10, the conveyor system 1400 places the tray 110 containing the batch of eggs 100 on the heating module 1100. In a step S20, the heating module 1100 exposes the batch of eggs 100 to a punctual and fast heat flux through a shortwave infrared light generated by the lamps 1110. The shortwave infrared light hits and warms up the second extremity 104b of each egg 100. The exposure of the batch of eggs 100 is performed through a punctual and fast heat flux to generate a hot zone generally confined in the air cell 102 of each egg 100. To generate such a hot zone inside the air cell 102, parameters of the heat flux such as the exposure period and an exposure temperature may be adjusted.

The predetermined exposure period and other parameters, such as the exposure distance D1, the nominal power of the lamps 1110, and the rate at which the tray 110 passes on top of the heating module 1100, the number of eggs per hour to be processed, are adjusted to generate a hot zone sufficiently hot to be detected from thermal images captured by the thermal camera 1210 while maintaining the temperatures of the other parts of the egg 100 substantially unchanged.

For example, the exposure period may be between 1 and 9 seconds for the at least one pair of lamps 1110 delivering a nominal power between 500 W and 5000 W, for example 1000 W, and being placed from the batch of eggs 100 at an exposure distance D1 between 60 mm and 200 mm. Preferably, an optimum energy production, i.e. the nominal power multiplied by the exposure period, may be between 400 J and 5000 J, an optimum temperature increase rate, i.e. ratio between the temperature increase of the hot zone and the exposure period, may be between 1° C./s and 15° C./s. In a non-limiting embodiment, the system can process the eggs at a cadence of about 30 000 eggs/h, using a tray speed of about 23 cm/s, a distance D1 of about 60 mm, and a power of 1500 W for each of a pair of lamps.

In a step S30, the conveyor system 1400 displaced the tray 110 containing the batch of eggs 100 from the top of the heating module 1100 to the top of the imaging module 1200.

In a step S40, the thermal camera 1210 captures thermal images of the batch of eggs 100. The thermal images captured contain the temperature distribution on the second extremity 104b of each egg 100 that have been exposed to shortwave infrared light emitted in the step S20, as well as an exposed part of the tray 110.

In a preferred embodiment steps S20 and S40 are performed without stopping the conveyor system and while the tray and eggs are moving. In a non-limiting embodiment, the conveyor system can be adjusted to slow down and/or accelerate the tray such that S20 and S40 can be performed while the tray is moving at different speeds. The conveyor system can also be adjusted to set the speed of the tray depending on the location of the tray.

In a step S50, upside down eggs 100*d* are detected by imaging the thermal images captured in the step S40, via software instructions executed by a processor 1302 of the analyzer module 1300.

The detection of upside down eggs 100*d* inside the batch of eggs 100 is performed by determining the presence or absence of the hot zone around the second extremity 104*b* of each egg 100.

If the presence of the hot zone around of the second extremity 104*b* is detected, the process concludes that the air cell 102 is located near the second extremity 104*b* and that the egg 100 is in an upside down position, as illustrated in FIG. 1 by the egg 100*d*.

Otherwise, if the absence of the hot zone around of the second extremity 104*b* is detected, the process concludes that the air cell 102 is located near the first extremity 104*a*, not the second extremity 104*b*, and that the egg 100 is in an upright position, as illustrated in FIG. 1 by the egg 100*u*.

The software instructions for the detection of the presence or absence of the hot zone may rely on the use of masks and/or filters to remove irrelevant parts present in the thermal images, e.g. exposed parts of the tray 110 or thermal noises.

The software instructions may also rely on computing a threshold value for the hot zone based on global statistical measurements, e.g. temperature variance across the whole batch of eggs 100, and local statistical measurements, e.g. temperature variance for each egg.

In addition, image processing tools, e.g. intensity differences and variations, edge detection, image segmentation, image enhancement, noise reduction, geometric transformations, or image registration, may also be used to detect the presence of air cell 102 as well as measure other characteristics of the egg 100 such as temperature and size of the air cell 102.

In a non-limiting preferred embodiment, the steps S10-S50 are performed before the incubation of the eggs. Conventionally, shortly after the eggs are laid by the chickens, the eggs are placed in a cooling chamber, where the temperature is between about 12° and 21° C., in order to stop or slow down their development. The eggs are later placed in an incubation chamber where the temperature is between about 35° and 38° C. The method according to a non-limiting preferred embodiment of the present invention is performed just before the incubation of the eggs, i.e., the heating module 1100 and the imaging modules 1200 are placed between the cooling chamber and the incubation chamber.

Figure 5:
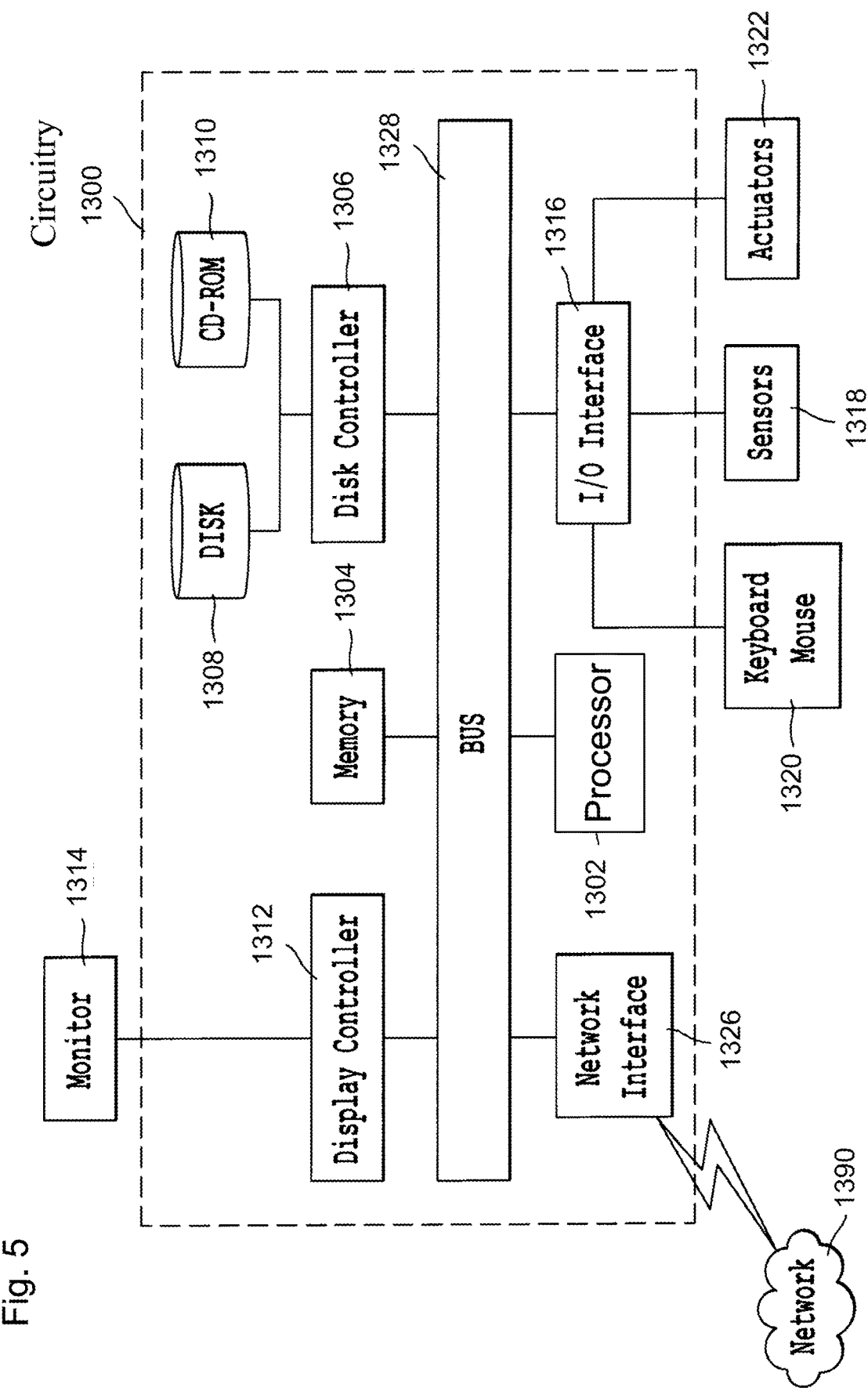
FIG. 5 is a schematic view of a hardware diagram of an analyzer module of the imaging module, according to certain aspects of the disclosure.

FIG. 5 a schematic view of a hardware diagram of the control module 1300 of the apparatus 1000, according to certain aspects of the disclosure.

As shown in FIG. 5, systems, operations, and processes in accordance with this disclosure may be implemented using the processor 1302 or at least one application specific processor (ASP). The processor 1302 may utilize a computer readable storage medium, such as a memory 1304 (e.g. ROM, EPROM, EEPROM, flash memory, static memory, DRAM SDRAM, and their equivalents), configured to control the processor 1302 to perform and/or control the systems, operations, and processes of this disclosure. In addition, the memory 1304 may be used to store the thermal images of the batch of eggs 100 taken by the thermal camera 1210. Other storage mediums may be controlled via a controller, such as a disk controller 1306, which may control a hard disk drive 1308 or optical disk drive 1310.

The processor 1302 or aspects thereof, in an alternate embodiment, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The processor 1302 may be a separate device or a single processing mechanism. Further, this disclosure may benefit form parallel processing capabilities of a multi-cored processor. In another aspect, results of processing in accordance with this disclosure may be displayed via a display controller 1312 to a monitor 1314 that may be peripheral to or part of the control module 1300. The monitor 1314 may be used to display thermal pictures of the batch of eggs 100 taken by the thermal camera 1210, as illustrated in FIG. 1. Moreover, the monitor 1314 may be provided with a touch-sensitive interface to a command/instruction interface. The display controller 1312 may also include at least one graphic processing unit for improved computational efficiency. Additionally, the control module 1300 may include an I/O (input/output) interface 1316, provided for inputting sensor data from sensors 1318 and for outputting orders to actuators 1322. The sensors 1318 and actuators are illustrative of any of the sensors and actuators described in this disclosure, such as the thermal camera 1210.

Further, other input devices may be connected to the I/O interface 1316 as peripherals or as part of the control module 1300. For example, a keyboard or a pointing device such as a mouse 1320 may control parameters of the various processes and algorithms of this disclosure, and may be connected to the I/O interface 1316 to provide additional functionality and configuration options, or to control display characteristics. Actuators 1322 which may be embodied in any of the elements of the automatic apparatuses described in this disclosure may also be connected to the I/O interface 1316. The above-noted hardware components may be coupled to the network 1324 via a network interface 1326 for the transmission or reception of data, including controllable parameters. A central BUS 1328 may be provided to connect the above-noted hardware components together, and to provide at least one path for digital communication there between.

The foregoing discussion discloses and describes merely exemplary embodiments of an object of the present disclosure. As will be understood by those skilled in the art, an object of the present disclosure may be embodied in other specific forms without departing from the spirit or essential characteristics thereof. Accordingly, the present disclosure is intended to be illustrative, but not limiting of the scope of an object of the present disclosure as well as the claims.

Numerous modifications and variations on the present invention are possible in light of the above teachings. It is therefore to be understood that within the scope of the appended claims, the invention may be practiced otherwise than as specifically described herein.

What is claimed is:

1. An apparatus to identify an orientation of each egg of a batch of eggs, each egg of the batch being in a fixed position defining a first extremity and a second extremity of the egg, each egg having an air cell that is located either in the first extremity or the second extremity, the location of the air cell in one of the first extremity or the second extremity defining an upside-down position of the egg the apparatus comprising:
- a heating module comprising an infrared light source configured to expose the batch of eggs to an infrared light and create a hot zone in the air cell of any upside-down egg, the infrared light source comprising an infrared coated lamp that emits shortwave infrared light;
- an imaging module with a thermal camera configured to capture thermal images of the batch of eggs; and
- an analyzer module configured to detect presence of the hot zone in the air cell of any upside-down egg from the thermal images and identify the orientation of each egg in the batch of eggs.

2. The apparatus of claim 1, wherein the infrared light source comprises a reflector configured to limit heat waste and to direct the shortwave infrared light towards the batch of eggs.

3. The apparatus of claim 1, wherein the exposure period is between 1 and 9 seconds and the exposure distance is between 60 mm and 200 mm.

4. The apparatus of claim 1, wherein the heating module further comprises a screen configured to protect the infrared light source from debris from the batch of eggs.

5. The apparatus of claim 4, wherein the screen is transparent to infrared.

6. The apparatus of claim 5, wherein the screen is made from a mixture of silica and quartz.

7. The apparatus of claim 1, wherein the heating module further comprises a cooling system configured to cool the infrared light source.

8. The apparatus of claim 7, wherein the cooling system comprises a fan configured to extract air from the infrared light source and away from the batch of eggs and the imaging module.

9. An apparatus to identify upside-down eggs of a batch of eggs, comprising:
- a heating module configured to expose each egg of the batch of eggs to a radiation flux, the heating module comprising an infrared coated lamp that emits shortwave infrared light,
- an imaging module with a thermal camera configured to capture thermal images of the batch of eggs when the eggs are not exposed to the radiation flux; and
- an analyzer module configured to detect presence of a heated zone in an air cell of any upside-down egg from the thermal images and identify upside-down eggs based on the presence of the heated zone.

10. The apparatus of claim 9, wherein the imaging module further comprises an insulated housing to limit heat loss between the batch of eggs and the thermal camera.

11. The apparatus of claim 9, wherein the thermal camera is enclosed in a camera housing configured to protect the thermal camera from external elements.

12. The apparatus of claim 11, wherein the camera housing is made of heat conductor materials to extract heat from the thermal camera.

13. The apparatus of claim 11, wherein the camera housing includes a cooling system.

14. The apparatus of claim 9, wherein the analyzer module is configured to perform global and local statistical measurements on the thermal images to detect the hot zone.

15. A method to identify upside-down eggs from a batch of eggs, comprising:
- heating the batch of eggs with a radiation source, the radiation source comprising an infrared coated lamp that emits shortwave infrared light;
- generating a hot zone inside an air cell of any upside-down egg via the radiation source;
- stopping the heating of the batch of eggs with the radiation source;
- capturing thermal images of the batch of eggs with a thermal camera while the heating of the batch of eggs is stopped;
- analyzing the thermal images to detect presence of the hot zone; and
- identifying the upside-down eggs.

16. The method of claim 15, wherein the heating of the batch of eggs comprises emitting an infrared light on the batch of eggs during an exposure period, at a nominal power, and from an exposure distance.

17. The method of claim 16, wherein the exposure period is between 1 and 9 seconds, the nominal power between 1000 w and 5000 w, and the exposure distance is between 60 mm and 200 mm.

18. The method of claim 17, wherein the generating of the heat zone is performed so as to not significantly heat the rest of each egg.

19. The method of claim 18, wherein the stopping of the heating is performed by moving the eggs away from the radiation source.

20. The method of claim 19, wherein the heating, the generating and the capturing are performed while moving the eggs with a conveyor system configured to move the eggs from a location where the eggs are exposed to the radiation source to another location where the eggs are exposed to the thermal camera.

21. The method of claim 19, wherein the heating, the generating and the capturing are performed before incubation of the eggs.

* * * * *